(12) United States Patent
Napier et al.

(10) Patent No.: US 7,554,008 B2
(45) Date of Patent: Jun. 30, 2009

(54) Δ6-DESATURASES FROM PRIMULACEAE, EXPRESSING PLANTS AND PUFA-CONTAINING OILS

(75) Inventors: Johnathan A. Napier, Bristol (GB); Olga Sayanova, Harpenden (GB)

(73) Assignee: IACR-Rothamsted (GB)

( * ) Notice: Subject to any disclaimer, the term of this patent is extended or adjusted under 35 U.S.C. 154(b) by 528 days.

(21) Appl. No.: 10/504,424

(22) PCT Filed: Feb. 6, 2003

(86) PCT No.: PCT/EP03/01161

§ 371 (c)(1), (2), (4) Date: Aug. 13, 2004

(87) PCT Pub. No.: WO03/072784

PCT Pub. Date: Sep. 4, 2003

(65) Prior Publication Data

US 2005/0089865 A1    Apr. 28, 2005

(30) Foreign Application Priority Data

Feb. 27, 2002    (GB)    ................... 0204676.1

(51) Int. Cl.
- A01H 5/00    (2006.01)
- C12N 15/82    (2006.01)
- C07H 21/04    (2006.01)

(52) U.S. Cl. ..................... 800/298; 800/281; 536/23.2; 435/320.1

(58) Field of Classification Search .................. None
See application file for complete search history.

(56) References Cited

FOREIGN PATENT DOCUMENTS

WO    WO-96/21022 A2    7/1996
WO    WO-99/64614    12/1999

OTHER PUBLICATIONS

Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
De Luca, V, AgBiotech News and Information 5(6): 225N-229N, 1993.*
Wille et al., "Re-esterification of Polyunsaturated Fatty Acid Concentrates," *Fett Wissenschaft Technologie*, (1987), vol. 89, No. 12, pp. 480-485.
Infante et al., "Analysis of the putative role of 24-carbon polyunsaturated fatty acids in the biosynthesis of docosapentaenoic (22:5n-6) and docosahexaenoic (22:6n-3) acids," *FEBS Letters*, (1998), vol. 431, No. 1, pp. 1-6.
Sayanova et al., "$\Delta^6$-Unsaturated fatty acids in species and tissues of the Primulaceae," *Phytochemistry*, (1999), vol. 52, No. 3, pp. 419-422.
De Antueno et al., "Activity of human Δ5 and Δ6 desaturases on multiple n-3 and n-6 polyunsaturated fatty acids," *FEBS Letters*, (2001), pp. 77-80, vol. 509, No. 1, Elsevier Science Publishers, Amsterdam, NL, XP004329147.
Sayanova et al., "Identification of *Primula* fatty acid Δ6-desaturases with *n*-3 substrate preferences," *FEBS Letters*, (2003), vol. 542, No. 1, pp. 100-104.

* cited by examiner

*Primary Examiner*—Elizabeth F McElwain
(74) *Attorney, Agent, or Firm*—Connolly Bove Lodge & Hutz LLP

(57) ABSTRACT

The present invention relates to an improved method for the specific production of unsaturated ω-3 fatty acids and a method for the production of triglycerides having an increased content of unsaturated fatty acids, in particular ω-3 fatty acids having more than three double bonds. The invention relates to the production of a transgenic organism, preferably a transgenic plant or a transgenic microorganism, having an increased content of fatty acids, oils or lipids having Δ6 double bonds due to the expression of a Δ6-desaturase from Primulaceae. The invention additionally relates to expression cassettes containing a nucleic acid sequence, a vector and organisms containing at least one nucleic acid sequence or an expression cassette. The invention further relates to unsaturated fatty acids and triglycerides having an increased content of unsaturated fatty acids and use thereof.

50 Claims, No Drawings

SEQUENCE LISTING

<160> NUMBER OF SEQ ID NOS: 4

<210> SEQ ID NO 1
<211> LENGTH: 1362
<212> TYPE: DNA
<213> ORGANISM: Aleuritia farinosa
<220> FEATURE:
<221> NAME/KEY: CDS
<222> LOCATION: (1)..(1362)

<400> SEQUENCE: 1

```
atg gct aac aaa tct cca cca aac ccc aaa aca ggt tac ata acc agc       48
Met Ala Asn Lys Ser Pro Pro Asn Pro Lys Thr Gly Tyr Ile Thr Ser
 1               5                  10                  15 tca gac ctg aaa tcc cac aac aag gca ggt gac cta tgg ata tca atc       96
Ser Asp Leu Lys Ser His Asn Lys Ala Gly Asp Leu Trp Ile Ser Ile
             20                  25                  30 cac ggc caa gtc tac gac gtg tcc tct tgg gcc gcc ctt cat ccg ggg      144
His Gly Gln Val Tyr Asp Val Ser Ser Trp Ala Ala Leu His Pro Gly
         35                  40                  45 ggc act gcc cct ctc atg gcc ctt gca gga cac gac gtg acc gat gct      192
Gly Thr Ala Pro Leu Met Ala Leu Ala Gly His Asp Val Thr Asp Ala
     50                  55                  60 ttc ctc gcg tac cat ccc cct tcc act gcc cgt ctc ctc cct cct ctc      240
Phe Leu Ala Tyr His Pro Pro Ser Thr Ala Arg Leu Leu Pro Pro Leu
 65                  70                  75                  80 tct acc aac ctc ctt ctt caa aac cac tcc gtc tcc ccc acc tcc tca      288
Ser Thr Asn Leu Leu Leu Gln Asn His Ser Val Ser Pro Thr Ser Ser
                 85                  90                  95 gac tac cgc aaa ctc ctc gac aac ttc cat aaa cat ggc ctt ttc cgc      336
Asp Tyr Arg Lys Leu Leu Asp Asn Phe His Lys His Gly Leu Phe Arg
            100                 105                 110 gcc agg ggc cac act gct tac gcc acc ttc gtc ttc atg ata gcg atg      384
Ala Arg Gly His Thr Ala Tyr Ala Thr Phe Val Phe Met Ile Ala Met
        115                 120                 125 ttt cta atg agc gtg act gga gtc ctt tgc agc gac agt gcg tgg gtc      432
Phe Leu Met Ser Val Thr Gly Val Leu Cys Ser Asp Ser Ala Trp Val
```

-continued

```
            130                 135                 140
cat ttg gct agc ggc gga gca atg ggg ttc gcc tgg atc caa tgc gga         480
His Leu Ala Ser Gly Gly Ala Met Gly Phe Ala Trp Ile Gln Cys Gly
145                 150                 155                 160 tgg ata ggt cac gac tct ggg cat tac cgg att atg tct gac agg aaa         528
Trp Ile Gly His Asp Ser Gly His Tyr Arg Ile Met Ser Asp Arg Lys
                165                 170                 175 tgg aac tgg ttc gcg caa atc cta agc aca aac tgc ctc cag ggg att         576
Trp Asn Trp Phe Ala Gln Ile Leu Ser Thr Asn Cys Leu Gln Gly Ile
        180                 185                 190 agt atc ggg tgg tgg aag tgg aac cat aat gcg cac cac atc gct tgc         624
Ser Ile Gly Trp Trp Lys Trp Asn His Asn Ala His His Ile Ala Cys
    195                 200                 205 aat agc ctg gat tac gac ccc gac ctc cag tat atc cct ttg ctc gtc         672
Asn Ser Leu Asp Tyr Asp Pro Asp Leu Gln Tyr Ile Pro Leu Leu Val
210                 215                 220 gtc tcc ccc aag ttc ttc aac tcc ctt act tct cgt ttc tac gac aag         720
Val Ser Pro Lys Phe Phe Asn Ser Leu Thr Ser Arg Phe Tyr Asp Lys
225                 230                 235                 240 aag ctg aac ttc gac ggc gtg tcg agg ttt ctg gtt tgc tac cag cac         768
Lys Leu Asn Phe Asp Gly Val Ser Arg Phe Leu Val Cys Tyr Gln His
                245                 250                 255 tgg acg ttt tat ccg gtc atg tgt gtc gct agg ctg aac atg ctc gcg         816
Trp Thr Phe Tyr Pro Val Met Cys Val Ala Arg Leu Asn Met Leu Ala
        260                 265                 270 cag tca ttt ata acg ctt ttc tcg agt agg gag gtg tgc cat agg gcg         864
Gln Ser Phe Ile Thr Leu Phe Ser Ser Arg Glu Val Cys His Arg Ala
    275                 280                 285 caa gag gtt ttc gga ctt gcc gtg ttt tgg gtt tgg ttt ccg ctt tta         912
Gln Glu Val Phe Gly Leu Ala Val Phe Trp Val Trp Phe Pro Leu Leu
290                 295                 300 ctt tct tgt tta cct aat tgg ggc gag agg att atg ttt ttg ctt gcg         960
Leu Ser Cys Leu Pro Asn Trp Gly Glu Arg Ile Met Phe Leu Leu Ala
305                 310                 315                 320 agc tat tcc gtt acg ggg ata caa cac gtg cag ttc agc ttg aac cat        1008
Ser Tyr Ser Val Thr Gly Ile Gln His Val Gln Phe Ser Leu Asn His
                325                 330                 335 ttt tct tcg gac gtc tat gtg ggc ccg cca gta ggt aat gac tgg ttc        1056
Phe Ser Ser Asp Val Tyr Val Gly Pro Pro Val Gly Asn Asp Trp Phe
        340                 345                 350 aag aaa cag act gcc ggg aca ctt aac ata tcg tgc ccg gcg tgg atg        1104
Lys Lys Gln Thr Ala Gly Thr Leu Asn Ile Ser Cys Pro Ala Trp Met
    355                 360                 365 gat tgg ttc cat ggc ggg tta cag ttt cag gtc gag cac cac ttg ttt        1152
Asp Trp Phe His Gly Gly Leu Gln Phe Gln Val Glu His His Leu Phe
370                 375                 380 ccg cgg atg cct agg ggt cag ttt agg aag att tct cct ttt gtg agg        1200
Pro Arg Met Pro Arg Gly Gln Phe Arg Lys Ile Ser Pro Phe Val Arg
385                 390                 395                 400 gat ttg tgt aag aaa cac aac ttg cct tac aat atc gcg tct ttt act        1248
Asp Leu Cys Lys Lys His Asn Leu Pro Tyr Asn Ile Ala Ser Phe Thr
                405                 410                 415 aaa gcg aat gtg ttt acg ctt aag acg ctg aga aat acg gcc att gag        1296
Lys Ala Asn Val Phe Thr Leu Lys Thr Leu Arg Asn Thr Ala Ile Glu
        420                 425                 430 gct cgg gac ctc tct aat ccg ctc cca aag aat atg gtg tgg gaa gct        1344
Ala Arg Asp Leu Ser Asn Pro Leu Pro Lys Asn Met Val Trp Glu Ala
    435                 440                 445 ctt aaa act ctc ggg tga                                                1362
```

Leu Lys Thr Leu Gly
        450

<210> SEQ ID NO 2
<211> LENGTH: 453
<212> TYPE: PRT
<213> ORGANISM: Aleuritia farinosa

<400> SEQUENCE: 2

Met Ala Asn Lys Ser Pro Pro Asn Pro Lys Thr Gly Tyr Ile Thr Ser
  1               5                  10                  15

Ser Asp Leu Lys Ser His Asn Lys Ala Gly Asp Leu Trp Ile Ser Ile
             20                  25                  30

His Gly Gln Val Tyr Asp Val Ser Ser Trp Ala Ala Leu His Pro Gly
         35                  40                  45

Gly Thr Ala Pro Leu Met Ala Leu Ala Gly His Asp Val Thr Asp Ala
     50                  55                  60

Phe Leu Ala Tyr His Pro Pro Ser Thr Ala Arg Leu Leu Pro Pro Leu
 65                  70                  75                  80

Ser Thr Asn Leu Leu Gln Asn His Ser Val Ser Pro Thr Ser Ser
             85                  90                  95

Asp Tyr Arg Lys Leu Leu Asp Asn Phe His Lys His Gly Leu Phe Arg
            100                 105                 110

Ala Arg Gly His Thr Ala Tyr Ala Thr Phe Val Phe Met Ile Ala Met
        115                 120                 125

Phe Leu Met Ser Val Thr Gly Val Leu Cys Ser Asp Ser Ala Trp Val
130                 135                 140

His Leu Ala Ser Gly Gly Ala Met Gly Phe Ala Trp Ile Gln Cys Gly
145                 150                 155                 160

Trp Ile Gly His Asp Ser Gly His Tyr Arg Ile Met Ser Asp Arg Lys
                165                 170                 175

Trp Asn Trp Phe Ala Gln Ile Leu Ser Thr Asn Cys Leu Gln Gly Ile
            180                 185                 190

Ser Ile Gly Trp Trp Lys Trp Asn His Asn Ala His His Ile Ala Cys
        195                 200                 205

Asn Ser Leu Asp Tyr Asp Pro Asp Leu Gln Tyr Ile Pro Leu Leu Val
    210                 215                 220

Val Ser Pro Lys Phe Phe Asn Ser Leu Thr Ser Arg Phe Tyr Asp Lys
225                 230                 235                 240

Lys Leu Asn Phe Asp Gly Val Ser Arg Phe Leu Val Cys Tyr Gln His
                245                 250                 255

Trp Thr Phe Tyr Pro Val Met Cys Val Ala Arg Leu Asn Met Leu Ala
            260                 265                 270

Gln Ser Phe Ile Thr Leu Phe Ser Arg Glu Val Cys His Arg Ala
        275                 280                 285

Gln Glu Val Phe Gly Leu Ala Val Phe Trp Val Trp Phe Pro Leu Leu
    290                 295                 300

Leu Ser Cys Leu Pro Asn Trp Gly Glu Arg Ile Met Phe Leu Leu Ala
305                 310                 315                 320

Ser Tyr Ser Val Thr Gly Ile Gln His Val Gln Phe Ser Leu Asn His
                325                 330                 335

Phe Ser Ser Asp Val Tyr Val Gly Pro Pro Val Gly Asn Asp Trp Phe
            340                 345                 350

Lys Lys Gln Thr Ala Gly Thr Leu Asn Ile Ser Cys Pro Ala Trp Met
        355                 360                 365

```
Asp Trp Phe His Gly Gly Leu Gln Phe Gln Val Glu His His Leu Phe
    370                 375                 380

Pro Arg Met Pro Arg Gly Gln Phe Arg Lys Ile Ser Pro Phe Val Arg
385                 390                 395                 400

Asp Leu Cys Lys Lys His Asn Leu Pro Tyr Asn Ile Ala Ser Phe Thr
                405                 410                 415

Lys Ala Asn Val Phe Thr Leu Lys Thr Leu Arg Asn Thr Ala Ile Glu
            420                 425                 430

Ala Arg Asp Leu Ser Asn Pro Leu Pro Lys Asn Met Val Trp Glu Ala
        435                 440                 445

Leu Lys Thr Leu Gly
    450

<210> SEQ ID NO 3
<211> LENGTH: 1362
<212> TYPE: DNA
<213> ORGANISM: Muscarioides vialii
<220> FEATURE:
<221> NAME/KEY: CDS
<222> LOCATION: (1)..(1362)

<400> SEQUENCE: 3 atg gct aac aaa tct cca cca aac ccc aaa aca ggt tac att acc agc       48
Met Ala Asn Lys Ser Pro Pro Asn Pro Lys Thr Gly Tyr Ile Thr Ser
1               5                   10                  15 tca gac ctg aaa ggg cac aac aaa gca gga gac cta tgg ata tca atc       96
Ser Asp Leu Lys Gly His Asn Lys Ala Gly Asp Leu Trp Ile Ser Ile
                20                  25                  30 cac ggg gag gta tac gac gtg tcc tcg tgg gcc ggc ctt cac ccg ggg      144
His Gly Glu Val Tyr Asp Val Ser Ser Trp Ala Gly Leu His Pro Gly
            35                  40                  45 ggc agt gcc ccc ctc atg gcc ctc gca gga cac gac gta acc gac gct      192
Gly Ser Ala Pro Leu Met Ala Leu Ala Gly His Asp Val Thr Asp Ala
        50                  55                  60 ttt cta gcg tat cat cct cct tct acc gcc cgc ctc ctc cct ccc ctc      240
Phe Leu Ala Tyr His Pro Pro Ser Thr Ala Arg Leu Leu Pro Pro Leu
65                  70                  75                  80 tcc acc aac ctc ctc ctt caa aac cac tcc gtc tcc ccc acc tcc tct      288
Ser Thr Asn Leu Leu Leu Gln Asn His Ser Val Ser Pro Thr Ser Ser
                85                  90                  95 gac tac cgc aaa ctc ctc cac aac ttc cat aaa att ggt atg ttc cgc      336
Asp Tyr Arg Lys Leu Leu His Asn Phe His Lys Ile Gly Met Phe Arg
                100                 105                 110 gcc agg ggc cac act gct tac gcc acc ttc gtc atc atg ata gtg atg      384
Ala Arg Gly His Thr Ala Tyr Ala Thr Phe Val Ile Met Ile Val Met
            115                 120                 125 ttt cta acg agc gtg acc gga gtc ctt tgc agc gac agt gcg tgg gtc      432
Phe Leu Thr Ser Val Thr Gly Val Leu Cys Ser Asp Ser Ala Trp Val
        130                 135                 140 cat ctg gct agc ggc gca gca atg ggg ttc gcc tgg atc cag tgc gga      480
His Leu Ala Ser Gly Ala Ala Met Gly Phe Ala Trp Ile Gln Cys Gly
145                 150                 155                 160 tgg ata ggt cac gac tct ggg cat tac cgg att atg tct gac agg aaa      528
Trp Ile Gly His Asp Ser Gly His Tyr Arg Ile Met Ser Asp Arg Lys
                165                 170                 175 tgg aac tgg ttc gcg cag gtc ctg agc aca aac tgc ctc cag ggg atc      576
Trp Asn Trp Phe Ala Gln Val Leu Ser Thr Asn Cys Leu Gln Gly Ile
                180                 185                 190 agt atc ggg tgg tgg aag tgg aac cat aac gcc cac cac att gct tgc      624
```

```
Ser Ile Gly Trp Trp Lys Trp Asn His Asn Ala His His Ile Ala Cys
        195                 200                 205 aat agc ctg gac tac gac ccc gac ctc cag tat atc cct ttg ctc gtg      672
Asn Ser Leu Asp Tyr Asp Pro Asp Leu Gln Tyr Ile Pro Leu Leu Val
210                 215                 220 gtc tcc ccc aag ttc ttc aac tcc ctt act tct cgt ttc tac gac aag      720
Val Ser Pro Lys Phe Phe Asn Ser Leu Thr Ser Arg Phe Tyr Asp Lys
225                 230                 235                 240 aag ctg aat ttc gac ggc gtg tca agg ttt ctg gtt tgc tac cag cac      768
Lys Leu Asn Phe Asp Gly Val Ser Arg Phe Leu Val Cys Tyr Gln His
        245                 250                 255 tgg acg ttt tat cca gtc atg tgt gtc gct agg cta aac atg atc gca      816
Trp Thr Phe Tyr Pro Val Met Cys Val Ala Arg Leu Asn Met Ile Ala
        260                 265                 270 cag tcg ttt ata acg ctt ttc tcg agc agg gag gtg ggt cat agg gcg      864
Gln Ser Phe Ile Thr Leu Phe Ser Ser Arg Glu Val Gly His Arg Ala
        275                 280                 285 caa gag att ttc gga ctt gct gtg ttt tgg gtt tgg ttt ccg ctc ctg      912
Gln Glu Ile Phe Gly Leu Ala Val Phe Trp Val Trp Phe Pro Leu Leu
290                 295                 300 ctc tct tgc tta cct aat tgg agc gag agg att atg ttt ctg cta gcg      960
Leu Ser Cys Leu Pro Asn Trp Ser Glu Arg Ile Met Phe Leu Leu Ala
305                 310                 315                 320 agc tat tcc gtt acg ggg ata cag cac gtg cag ttc agc ttg aac cat     1008
Ser Tyr Ser Val Thr Gly Ile Gln His Val Gln Phe Ser Leu Asn His
        325                 330                 335 ttt tct tcg gac gtc tac gtg ggc ccg cca gta ggt aac gac tgg ttc     1056
Phe Ser Ser Asp Val Tyr Val Gly Pro Pro Val Gly Asn Asp Trp Phe
        340                 345                 350 aag aaa cag act gct ggg aca ctt aac ata tcg tgc ccg gcg tgg atg     1104
Lys Lys Gln Thr Ala Gly Thr Leu Asn Ile Ser Cys Pro Ala Trp Met
        355                 360                 365 gac tgg ttc cat ggc ggg ttg cag ttt cag gtc gag cac cac ttg ttt     1152
Asp Trp Phe His Gly Gly Leu Gln Phe Gln Val Glu His His Leu Phe
        370                 375                 380 ccg cgg atg cct agg ggt cag ttt agg aag att tct cct ttt gtg agg     1200
Pro Arg Met Pro Arg Gly Gln Phe Arg Lys Ile Ser Pro Phe Val Arg
385                 390                 395                 400 gat ttg tgt aag aaa cac aac ttg cct tac aat atc gcg tct ttt act     1248
Asp Leu Cys Lys Lys His Asn Leu Pro Tyr Asn Ile Ala Ser Phe Thr
                405                 410                 415 aaa gca aac gtg ttg acg ctt aag acg ctg aga aat acg gcc att gag     1296
Lys Ala Asn Val Leu Thr Leu Lys Thr Leu Arg Asn Thr Ala Ile Glu
        420                 425                 430 gct cgg gac ctc tct aat ccg acc cca aag aat atg gtg tgg gaa gcc     1344
Ala Arg Asp Leu Ser Asn Pro Thr Pro Lys Asn Met Val Trp Glu Ala
        435                 440                 445 gtc cac aca cac ggc tag                                             1362
Val His Thr His Gly
        450

<210> SEQ ID NO 4
<211> LENGTH: 453
<212> TYPE: PRT
<213> ORGANISM: Muscarioides vialii

<400> SEQUENCE: 4

Met Ala Asn Lys Ser Pro Pro Asn Pro Lys Thr Gly Tyr Ile Thr Ser
1               5                   10                  15

Ser Asp Leu Lys Gly His Asn Lys Ala Gly Asp Leu Trp Ile Ser Ile
```

```
                  20                  25                  30
His Gly Glu Val Tyr Asp Val Ser Ser Trp Ala Gly Leu His Pro Gly
         35                  40                  45
Gly Ser Ala Pro Leu Met Ala Leu Ala Gly His Asp Val Thr Asp Ala
     50                  55                  60
Phe Leu Ala Tyr His Pro Pro Ser Thr Ala Arg Leu Leu Pro Pro Leu
 65                  70                  75                  80
Ser Thr Asn Leu Leu Leu Gln Asn His Ser Val Ser Pro Thr Ser Ser
                 85                  90                  95
Asp Tyr Arg Lys Leu Leu His Asn Phe His Lys Ile Gly Met Phe Arg
            100                 105                 110
Ala Arg Gly His Thr Ala Tyr Ala Thr Phe Val Ile Met Ile Val Met
        115                 120                 125
Phe Leu Thr Ser Val Thr Gly Val Leu Cys Ser Asp Ser Ala Trp Val
    130                 135                 140
His Leu Ala Ser Gly Ala Ala Met Gly Phe Ala Trp Ile Gln Cys Gly
145                 150                 155                 160
Trp Ile Gly His Asp Ser Gly His Tyr Arg Ile Met Ser Asp Arg Lys
                165                 170                 175
Trp Asn Trp Phe Ala Gln Val Leu Ser Thr Asn Cys Leu Gln Gly Ile
            180                 185                 190
Ser Ile Gly Trp Trp Lys Trp Asn His Asn Ala His His Ile Ala Cys
        195                 200                 205
Asn Ser Leu Asp Tyr Asp Pro Asp Leu Gln Tyr Ile Pro Leu Leu Val
    210                 215                 220
Val Ser Pro Lys Phe Phe Asn Ser Leu Thr Ser Arg Phe Tyr Asp Lys
225                 230                 235                 240
Lys Leu Asn Phe Asp Gly Val Ser Arg Phe Leu Val Cys Tyr Gln His
                245                 250                 255
Trp Thr Phe Tyr Pro Val Met Cys Val Ala Arg Leu Asn Met Ile Ala
            260                 265                 270
Gln Ser Phe Ile Thr Leu Phe Ser Ser Arg Glu Val Gly His Arg Ala
        275                 280                 285
Gln Glu Ile Phe Gly Leu Ala Val Phe Trp Val Trp Phe Pro Leu Leu
    290                 295                 300
Leu Ser Cys Leu Pro Asn Trp Ser Glu Arg Ile Met Phe Leu Leu Ala
305                 310                 315                 320
Ser Tyr Ser Val Thr Gly Ile Gln His Val Gln Phe Ser Leu Asn His
                325                 330                 335
Phe Ser Ser Asp Val Tyr Val Gly Pro Pro Val Gly Asn Asp Trp Phe
            340                 345                 350
Lys Lys Gln Thr Ala Gly Thr Leu Asn Ile Ser Cys Pro Ala Trp Met
        355                 360                 365
Asp Trp Phe His Gly Gly Leu Gln Phe Gln Val Glu His His Leu Phe
    370                 375                 380
Pro Arg Met Pro Arg Gly Gln Phe Arg Lys Ile Ser Pro Phe Val Arg
385                 390                 395                 400
Asp Leu Cys Lys Lys His Asn Leu Pro Tyr Asn Ile Ala Ser Phe Thr
                405                 410                 415
Lys Ala Asn Val Leu Thr Leu Lys Thr Leu Arg Asn Thr Ala Ile Glu
            420                 425                 430
```

```
Ala Arg Asp Leu Ser Asn Pro Thr Pro Lys Asn Met Val Trp Glu Ala
            435                 440                 445
Val His Thr His Gly
    450
```

Δ6-DESATURASES FROM PRIMULACEAE, EXPRESSING PLANTS AND PUFA-CONTAINING OILS

RELATED APPLICATIONS

This application is a national stage application (under 35 U.S.C. 371) of PCT/EP2003/001161 filed Feb. 6, 2003, which claims benefit of United Kingdom application 0204676.1 filed Feb. 24, 2002.

FIELD OF THE INVENTION

The present invention relates to an improved method for the specific production of unsaturated ω-3 fatty acids and a method for the production of triglycerides having an increased content of unsaturated fatty acids, in particular ω-3 fatty acids having more than three double bonds. The invention relates to the production of a transgenic organism, preferably a transgenic plant or a transgenic microorganism, having an increased content of fatty acids, oils or lipids having Δ 6 double bonds due to the expression of a Δ 6-desaturase from Primulaceae.

The invention additionally relates to expression cassettes containing a nucleic acid sequence, a vector and organisms containing at least one nucleic acid sequence or an expression cassette. The invention further relates to unsaturated fatty acids and triglycerides having an increased content of unsaturated fatty acids and use thereof.

DESCRIPTION OF THE BACKGROUND

Fatty acids and triglycerides have numerous applications in the food industry, animal nutrition, cosmetics and in the drug sector. Depending on whether they are free saturated or unsaturated fatty acids or are triglycerides having an increased content of saturated or unsaturated fatty acids, they are suitable for the most varied applications. Thus, for example, polyunsaturated fatty acids are added to infant formula to increase its nutritional value. The various fatty acids and triglycerides are mainly obtained from microorganisms such as *Mortierella* or from oil-producing plants such as soybean, oilseed rape, sunflower and others, and generally occur in the form of their triacylglycerides. However, they may also be obtained from animals, e.g. fish. The free fatty acids are advantageously produced by saponification.

Depending on application purpose oils containing saturated or unsaturated fatty acids are preferred, thus in human nutrition for example, lipids containing unsaturated fatty acids, especially polyunsaturated fatty acids, are preferred since they have a positive effect on the level of cholesterol in the blood and hence on the possibility of heart disease. They are employed in various dietary foods or medicinal drugs.

On account of their positive properties there has been no shortage of attempts in the past to make available genes which participate in the synthesis of fatty acids or triglycerides for the production of oils in various organisms having a modified content of unsaturated fatty acids. Thus, in WO 91/13972 and its US equivalent a Δ 9-desaturase is described. In WO 93/11245 a Δ 15-desaturase and in WO 94/11516 a Δ 12-desaturase is claimed. Other desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. To date, however, the various desaturases have been only inadequately characterized biochemically since the enzymes in the form of membrane-bound proteins are isolable and characterizable only with very great difficulty (McKeon et al., Methods in Enzymol. 71, 1981: 12141-12147, Wang et al., Plant Physiol. Biochem., 26, 1988: 777-792). Generally, membrane-bound desaturases are characterized by introduction into a suitable organism which is then investigated for enzyme activity by means of analysis of starting materials and products. Δ 6-Desaturases are described in WO 93/06712, U.S. Pat. Nos. 5,614,393, 5,614,393, WO 96/21022, WO0021557 and WO 99/27111 and their application to production in transgenic organisms is also described, e.g. in WO 9846763, WO 9846764 and WO 9846765. At the same time the expression of various desaturases, as in WO 9964616 or WO 9846776, and the formation of polyunsaturated fatty acids is also described and claimed. With regard to the effectiveness of the expression of desaturases and their effect on the formation of polyunsaturated fatty acids it may be noted that through expression of a single desaturase as described to date only low contents of Δ 6 unsaturated fatty acids/lipids, such as by way of example gamma-linolenic acid and stearidonic acid, have been achieved. Furthermore, a mixture of ω-3 and ω-6 fatty acids was usually obtained since all Δ 6-desaturases described so far converted, for example, linoleic acid (ω-6 fatty acid) as well as α-linolenic acid (ω-3 fatty acid).

Accordingly, there is still a great demand for new and more suitable genes which encode enzymes which participate in the biosynthesis of unsaturated fatty acids and make it possible to produce certain fatty acids specifically on an industrial scale without unwanted byproducts forming. In the selection of genes for biosynthesis two characteristics above all are particularly important. On the one hand, there is as ever a need for improved processes for obtaining the highest possible contents of polyunsaturated fatty acids. On the other hand, the enzymes employed should be highly specific to a certain substrate since as far as possible unwanted byproducts must not be produced which might have negative or so far undiscovered physiological effects in humans or animals due to food/feed intake.

SUMMARY OF THE INVENTION

Accordingly, it is an object of the present invention to introduce further genes of desaturase enzymes for the synthesis of polyunsaturated fatty acids into the seeds of an oil seed and in doing so to prevent the production of unwanted byproducts. We have found that this object is achieved by the isolated nucleic acid sequences according to the invention which encode polypeptides having Δ 6-desaturase activity, wherein the Δ 6-desaturases encoded by the nucleic acid sequences specifically convert ω-3 fatty acids. This object was achieved in particular by cloning the isolated nucleic acid sequences according to the invention, wherein the nucleic acid sequences encode a polypeptide having Δ 6-desaturase activity, wherein the Δ 6-desaturases encoded by the nucleic acid sequences specifically convert ω-3 fatty acids selected from the group:

a) a nucleic acid sequence having the sequence depicted in SEQ ID NO: 1 or SEQ ID NO: 3, b) nucleic acid sequences which may be derived as a result of the degenerated genetic code from the encoding sequence contained in SEQ ID NO: 1 or SEQ ID NO: 3, c) derivatives of the nucleic acid sequence depicted in SEQ ID NO: 1 or SEQ ID NO: 3 which encode polypeptides using the amino acid sequences depicted in SEQ ID NO: 2 or SEQ ID NO: 4 and have at least 75% homology on the amino acid level with SEQ ID NO: 2 or SEQ ID NO: 4 and possess Δ 6-desaturase activity Other embodiments and advantages of the invention are set forth in part in the description, which follows, and in part, may be obvious from this description, or may be learned from the practice of the invention.

DESCRIPTION OF THE INVENTION

The nucleic acid sequences according to the invention which encode polypeptides having a Δ 6-desaturase activity and originate from plants, advantageously Primulaceae such as Muscariodides or Aleuritia are specific for the conversion of ω-3 fatty acids and thus they preferably convert by way of example α-linolenic acid and not linoleic acid when they are expressed in a heterologous system and both fatty acids are available in the organism. By this means e.g. stearidonic acid, eicosapentaenoic acid or docosahexaenoic acid are produced in the host organisms such as plants or microorganisms without formation of arachidonic acid. This results in an advantageous synthesis of fatty acids of the ω-3 fatty acid family, while ω-6 fatty acids are scarcely formed if they occur at all. The Δ 6-desaturases according to the invention exhibit a higher activity towards ω-3 fatty acids as compared to ω-6 fatty acids by at least the factor 1.5, advantageously by at the least the factor 2, preferably by at least the factor 3, particularly preferably by at least the factor 4 and most particularly preferably by at least the factor 5. Due to this specificity the formation of unwanted fatty acids can be suppressed or completely prevented.

By derivative(s) of the sequences according to the invention is meant, for example, functional homologues of the polypeptides or enzymes encoded by SEQ ID NO: 1 or SEQ ID NO: 3 which exhibit the same said specific enzymatic activity. This specific enzymatic activity allows advantageously the synthesis of unsaturated fatty acids having more than three double bonds in the fatty acid molecule. By unsaturated fatty acids is meant in what follows diunsaturated or polyunsaturated fatty acids which possess double bonds. The double bonds may be conjugated or nonconjugated. The said sequences encode enzymes which exhibit Δ 6-desaturase activity.

The enzyme according to the invention, Δ 6-desaturase, advantageously introduces a cis double bond into fatty acid residues of glycerolipids at position $C_6$-$C_7$ (see SEQ ID NO: 1 and SEQ ID NO: 3). The enzymes additionally have a Δ 6-desaturase activity which advantageously introduces exclusively a cis double bond into fatty acid residues of glycerolipids at position $C_6$-$C_7$. This activity is also possessed by the enzymes having the sequences specified in SEQ ID NO: 1 and NO: 3 which are monofunctional Δ 6-desaturases.

The nucleic acid sequence(s) according to the invention (for purposes of the application the singular encompasses the plural and vice versa) or fragments thereof may advantageously be used for isolating other genomic sequences via homology screening.

The said derivatives may be isolated, for example, from other organisms, eukaryotic organisms such as plants, especially mosses, dinoflagellates or fungi.

Allele variants include in particular functional variants obtainable by deletion, insertion or substitution of nucleotides in the sequences depicted in SEQ ID NO: 1 or SEQ ID NO: 3, the enzymatic activity of the derived synthesized proteins being retained.

Starting from the DNA sequence described in SEQ ID NO: 1 and SEQ ID NO: 3 or parts of said sequences such DNA sequences can be isolated using, for example, normal hybridization methods or the PCR technique from other eukaryotes such as those identified above for example. These DNA sequences hybridize under standard conditions with the said sequences. For hybridization use is advantageously made of short oligonucleotides of the conserved regions, for example, which can be determined by comparisons with other desaturase genes in the manner known to those skilled in the art. The histidine box sequences are advantageously employed. However, longer fragments of the nucleic acids according to the invention or the complete sequences may also be used for hybridization. Depending on the nucleic acid employed: oligonucleotide, longer fragment or complete sequence, or depending on which type of nucleic acid, DNA or RNA, is used for hybridization these standard conditions vary. Thus, for example, the melting temperatures of DNA:DNA hybrids are approximately 10° C. lower than those of DNA:RNA hybrids of the same length.

By standard conditions is meant, for example, depending on the nucleic acid in question temperatures between 42° C. and 58° C. in an aqueous buffer solution having a concentration of between 0.1 and 5×SSC (1×SSC=0.15 M NaCl, 15 mM sodium citrate, pH 7.2) or additionally in the presence of 50% formamide, such as by way of example 42° C. in 5×SSC, 50% formamide. Hybridization conditions for DNA:DNA hybrids are advantageously 0.1×SSC and temperatures between approximately 20° C. and 45° C., preferably between approximately 30° C. and 45° C. For DNA:RNA hybrids the hybridization conditions are advantageously 0.1× SSC and temperatures between approximately 30° C. and 55° C., preferably between approximately 45° C. and 55° C. These specified temperatures for hybridization are melting temperature values calculated by way of example for a nucleic acid having a length of approximately 100 nucleotides and a G+C content of 50% in the absence of formamide. The experimental conditions for DNA hybridization are described in relevant genetics textbooks such as by way of example Sambrook et al., "Molecular Cloning", Cold Spring Harbor Laboratory, 1989, and may be calculated by formulae known to those skilled in the art, for example as a function of the length of the nucleic acids, the nature of the hybrids or the G+C content. Those skilled in the art may draw on the following textbooks for further information on hybridization: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Furthermore, by derivatives is meant homologues of the sequences SEQ ID NO: 1 and NO: 3, for example eukaryotic homologues, truncated sequences, single-stranded DNA of the encoding and nonencoding DNA sequence or RNA of the encoding and nonencoding DNA sequence.

In addition, by homologues of the sequences SEQ ID NO: 1 and SEQ ID NO: 3 is meant derivatives such as by way of example promoter variants. These variants may be modified by one or more nucleotide exchanges, by insertion(s) and/or deletion(s) without, however, adversely affecting the functionality or efficiency of the promoters. Furthermore, the promoters can have their efficiency increased by altering their sequence or be completely replaced by more effective promoters even of foreign organisms.

By derivatives is also advantageously meant variants whose nucleotide sequence has been altered in the region from −1 to −2000 ahead of the start codon in such a way that the gene expression and/or the protein expression is modified, preferably increased. Furthermore, by derivatives is also meant variants which have been modified at the 3' end.

By derivatives is also meant the antisense DNAs which may be employed for inhibiting protein biosynthesis of the proteins according to the invention. These antisense DNAs are numbered among the nonfunctional derivatives according to the invention such as derivatives which exhibit no enzymatic activity. Other methods known to those skilled in the art for the production of nonfunctional derivatives are what is known as cosuppression, the use of ribozymes and introns and the RNAi method. Ribozymes are catalytic RNA molecules having ribonuclease activity which can chop single-stranded nucleic acids, such as mRNA, with which they are complementary. In this way, using these ribozymes (Haselhoff and Gerlach, Nature, 334, 1988: 585-591) mRNA transcripts can be catalytically cleaved and, thus, the translation of this mRNA is suppressed. Ribozymes of this type can be specially tailored to their purpose (U.S. Pat. Nos. 4,987,071; 5,116,742 and Bartel et al., Science 261, 1993: 1411-1418). By this means, with the aid of the antisense DNA, fatty acids, lipids or oils having an increased content of saturated fatty acids can be produced.

The nucleic acid sequence according to the invention which encodes a Δ 6-desaturase may be produced by synthesis or obtained naturally or contain a mixture of synthetic and natural DNA components as well as consist of various heterologous Δ 6-desaturase gene segments from different organisms. In general, synthetic nucleotide sequences are produced with codons which are preferred by the corresponding host organisms, plants for example. This usually results in optimum expression of the heterologous gene. These codons preferred by plants may be determined from codons having the highest protein frequency which are expressed in most of the plant species of interest. An example concerning *Corynebacterium glutamicum* is provided in Wada et al. (1992) *Nucleic Acids Res.* 20:2111-2118). Such experiments can be carried out using standard methods and are known to the person skilled in the art.

Functionally equivalent sequences which encode the Δ 6-desaturase gene are those derivatives of the sequence according to the invention which despite differing nucleotide sequence still possess the desired functions, that is to say the enzymatic activity and specific selectivity of the proteins. Thus, functional equivalents include naturally occurring variants of the sequences described herein as well as artificial ones, e.g. artificial nucleotide sequences adapted to the codon use of a plant which have been obtained by chemical synthesis.

In addition, artificial DNA sequences are suitable, provided, as described above, they mediate the desired property, for example an increase in the content of Δ 6 double bonds in fatty acids, oils or lipids in organisms such as in a plant by overexpression of the Δ 6-desaturase gene in crop plants. Such artificial DNA sequences can exhibit Δ 6-desaturase activity, for example by back-translation of proteins constructed by means of molecular modeling, or be determined by in vitro selection. Possible techniques for in vitro evolution of DNA to modify or improve the DNA sequences are described in Patten, P. A. et al., Current Opinion in Biotechnology 8, 724-733(1997) or in Moore, J. C. et al., Journal of Molecular Biology 272, 336-347 (1997). Particularly suitable are encoding DNA sequences which are obtained by back-translation of a polypeptide sequence in accordance with the codon use specific to the host plant. Those skilled in the art familiar with the methods of plant genetics can easily determine the specific codon use by computer analyses of other known genes of the plant to be transformed.

Other suitable equivalent nucleic acid sequences which may be mentioned are sequences that encode fusion proteins, a component of the fusion protein being a Δ 6-desaturase polypeptide or a functionally equivalent part thereof. The second part of the fusion protein can be, for example, another polypeptide having enzymatic activity or an antigenic polypeptide sequence by means of which it is possible to demonstrate Δ 6-desaturase expression (e.g. myc tag or his tag). Preferably, however, this is a regulatory protein sequence, such as by way of example a signal sequence for the endoplasmic reticulum (=ER) which directs the Δ 6-desaturase protein to the desired point of action, or regulatory sequences which influence the expression of the nucleic acid sequence according to the invention, such as promoters or terminators.

Advantageously, the Δ 6-desaturase genes in the method according to the invention may be combined with other genes for fatty acid biosynthesis. Examples of such genes are the acetyl transferases, other desaturases or elongases such as Δ 4-, Δ 5-, Δ 6- or Δ 8-desaturases or ω-3- and/or ω-6-specific desaturases such as Δ 12 (for $C_{18}$ fatty acids), Δ 15 (for $C_{18}$ fatty acids) or Δ 19 (for $C_{22}$ fatty acids) or such as Δ 5- or Δ 6-elongases. For in vivo and especially in vitro synthesis combination with e.g. NADH cytochrome B5 reductases which can take up or release reduction equivalents is advantageous.

By the amino acid sequences according to the invention is meant proteins which contain an amino acid sequence depicted in the sequences SEQ ID NO: 2 and SEQ ID NO: 4 or a sequence obtainable therefrom by substitution, inversion, insertion or deletion of one or more amino acid groups, the enzymatic activities of the proteins depicted in SEQ ID NO: 2 and NO: 4 being retained or not substantially reduced, that is they still possess the same enzymatic activity. By "not substantially reduced" or "the same enzymatic activity" is meant all enzymes which still exhibit at least 10%, preferably 20%, particularly preferably 30%, of the enzymatic activity of the initial enzyme obtained from the wild form of the said Primulaceae organism. In doing this, for example, certain amino acids may be replaced by others having similar physicochemical properties (space filling, basicity, hydrophobicity, etc.). For example, arginine residues are exchanged for lysine residues, valine residues for isoleucine residues or aspartic acid residues for glutamic acid residues. However, one or more amino acids may also be swapped in sequence, added or removed, or a plurality of these measures may be combined with one another.

By derivatives is also meant functional equivalents which in particular also contain natural or artificial mutations of an originally isolated sequence encoding Δ 6-desaturase which continue to exhibit the desired function, that is the enzymatic activity and substrate selectivity thereof is not substantially reduced. Mutations comprise substitutions, additions, deletions, exchanges or insertions of one or more nucleotide residues. Thus, for example, the present invention also encompasses those nucleotide sequences which are obtained by modification of the Δ 6-desaturase nucleotide sequence. The aim of such a modification may be, e.g., to further bound the encoding sequence contained therein or also, e.g., to insert further restriction enzyme interfaces.

Functional equivalents also include those variants whose function by comparison with the initial gene or gene fragment is weakened (=not substantially reduced) or reinforced (=enzyme activity higher than the activity of the initial enzyme, that is activity is higher than 100%, preferably higher than 110%, particularly preferably higher than 130%).

At the same time the nucleic acid sequence may, for example, advantageously be a DNA or cDNA sequence. Suitable encoding sequences for insertion into an expression cassette according to the invention include by way of example those which encode a Δ 6-desaturase with the sequences described above and lend the host the ability to overproduce fatty acids, oils or lipids having double bonds in the Δ 6 position, it being advantageous when at the same time ω-3 fatty acids having at least four double bonds are produced. These sequences may be of homologous or heterologous origin.

By the expression cassette (=nucleic acid construct or fragment or gene construct) according to the invention is meant the sequences specified in SEQ ID NO: 1 and SEQ ID NO:3 which result from the genetic code and/or functional or non-functional derivatives thereof which are functionally linked with one or more regulation signals advantageously to increase the gene expression and which control the expression of the encoding sequence in the host cell. These regulatory sequences should allow the selective expression of the genes and the protein expression. Depending on the host organism this may mean, for example, that the gene is expressed and/or overexpressed only after induction or that it is expressed and/or overexpressed immediately. Examples of these regulatory sequences are sequences to which inductors or repressors bind and in this way regulate the expression of the nucleic acid. In addition to these new regulation sequences or instead of these sequences the natural regulation of these sequences ahead of the actual structural genes may still be present and optionally have been genetically modified so that natural regulation was switched off and the expression of the genes increased. However, the gene construct can also be built up more simply, that is no additional regulation signals have been inserted ahead of the nucleic acid sequence or derivatives thereof and the natural promoter with its regulation has not been removed. Instead of this the natural regulation sequence was mutated in such a way that no further regulation ensues and/or the gene expression is heightened. These modified promoters in the form of part sequences (=promoter containing parts of the nucleic acid equences according to the invention) can also be brought on their own ahead of the natural gene to increase the activity. In addition, the gene construct may advantageously also contain one or more so-called enhancer sequences functionally linked to the romoter which allow enhanced expression of the nucleic acid sequence. At the 3' end of the DNA sequences additional advantageous sequences may also be inserted, such as further regulatory elements or terminators. The Δ 6-desaturase gene may be present in one or more copies in the expression cassette (=gene construct).

As described above, the regulatory sequences or factors can preferably positively influence and so increase the gene expression of the introduced genes. Thus, reinforcement of the regulatory elements advantageously on the transcription level may be effected by using powerful transcription signals such as promoters and/or enhancers. However, in addition reinforcement of translation is also possible, for example by improving the stability of the mRNA.

Suitable promoters in the expression cassette are in principle all promoters which can control the expression of foreign genes in organisms such as microorganisms like protozoa such as ciliates, algae such as green, brown, red or blue algae, bacteria such as gram-positive or gram-negative bacteria, yeasts such as *Saccharomyces, Pichia* or *Schizosaccharomyces* or fungi such as *Mortierella, Traustochytrium* or *Schizochytrium*, advantageously in plants or fungi. Use is preferably made in particular of plant promoters or promoters derived from a plant virus. Advantageous regulation sequences for the method according to the invention are found for example in promoters such as cos, tac, trp, tet, trp-tet, lpp, lac, lpp-lac, lacI$^{q-}$, T7, T5, T3, gal, trc, ara, SP6, λ-$P_R$ or in λ-$P_L$ promoters which are employed advantageously in gram-negative bacteria. Other advantageous regulation sequences are found, for example, in the gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21(1980) 285-294], SSU, OCS, lib4, STLS1, B33, nos (=Nopalin Synthase Promoter) or in the ubiquintin promoter. The expression cassette may also contain a chemically inducible promoter by means of which the expression of the exogenous Δ 6-desaturase gene in the organisms can be controlled advantageously in the plants at a particular time. Advantageous plant promoters of this type are by way of example the PRP1 promoter [Ward et al., Plant. Mol. Biol.22(1993), 361-366], a promoter inducible by benzenesulfonamide (EP 388186), a promoter inducible by tetracycline (Gatz et al., (1992) Plant J. 2,397-404), a promoter inducible by salicylic acid (WO 95/19443), a promoter inducible by abscisic acid (EP335528) and a promoter inducible by ethanol or cyclohexanone (WO93/21334). Other examples of plant promoters which can advantageously be used are the promoter of cytosolic FBPase from potato, the ST-LSI promoter from potato (Stockhaus et al., EMBO J. 8 (1989) 2445-245), the promoter of phosphoribosyl pyrophosphate amidotransferase from *Glycine max* (see also gene bank accession number U87999) or a nodiene-specific promoter as described in EP 249676. Particularly advantageous are those plant promoters which ensure expression in tissues or plant parts/organs in which fatty acid biosynthesis or the precursor stages thereof occurs, as in endosperm or in the developing embryo for example. Particularly noteworthy are advantageous promoters which ensure seed-specific expression such as by way of example the USP promoter or derivatives thereof, the LEB4 promoter, the phaseolin promoter or the napin promoter. The particularly advantageous USP promoter cited according to the invention or its derivatives mediate very early gene expression in seed development (Baeumlein et al., Mol Gen Genet, 1991, 225 (3): 459-67). Other advantageous seed-specific promoters which may be used for monocotylodonous or dicotylodonous plants are the promoters suitable for dicotylodons such as napin gene promoters, likewise cited by way of example, from oilseed rape (U.S. Pat. No. 5,608,152), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the leguminous B4 promoter (LeB4, Baeumlein et al., Plant J., 2, 2, 1992: 233-239) or promoters suitable for monocotylodons such as the promoters of the lpt2 or lpt1 gene in barley (WO 95/15389 and WO 95/23230) or the promoters of the barley hordeine gene, the rice glutelin gene, the rice oryzin gene, the rice prolamin gene, the wheat gliadin gene, the white glutelin gene, the corn zein gene, the oats glutelin gene, the sorghum kasirin gene or the rye secalin gene which are described in WO99/16890.

Furthermore, particularly preferred are those promoters which ensure the expression in tissues or plant parts in which, for example, the biosynthesis of fatty acids, oils and lipids or the precursor stages thereof takes place. Particularly noteworthy are promoters which ensure a seed-specific expression. Noteworthy are the promoter of the napin gene from oilseed rape (U.S. Pat. No. 5,608,152), the USP promoter from *Vicia faba* (USP=unknown seed protein, Baeumlein et al., Mol Gen Genet, 1991, 225 (3): 459-67), the promoter of the oleosin gene from *Arabidopsis* (WO98/45461), the phaseolin promoter (U.S. Pat. No. 5,504,200) or the promoter of the legumin B4 gene (LeB4; Baeumlein et al., 1992, Plant Journal, 2 (2): 233-9). Other promoters to be mentioned are that of the lpt2 or lpt1 gene from barley (WO95/15389 and WO95/23230) which mediate seed-specific expression in monocotyledonous plants.

As described above, the expression construct (=gene construct, nucleic acid construct) may contain yet other genes which are to be introduced into the organisms. These genes can be subject to separate regulation or be subject to the same regulation region as the Δ 6-desaturase gene. These genes are by way of example other biosynthesis genes, advantageously for fatty acid biosynthesis, which allow increased synthesis. Examples which may be mentioned are the genes for Δ 15-, Δ 12-, Δ 9-, Δ 6-, Δ 5-, Δ 4-desaturase, β-ketoacyl reductases, β-ketoacyl synthases, elongases or the various hydroxylases and acyl-ACP thioesterases. The desaturase genes are advantageously used in the nucleic acid construct.

In principle all natural promoters with their regulation sequences can be used like those named above for the expression cassette according to the invention and the method according to the invention. Over and above this, synthetic promoters may also advantageously be used.

In the preparation of an expression cassette various DNA fragments can be manipulated in order to obtain a nucleotide sequence which usefully reads in the correct direction and is equipped with a correct reading raster. To connect the DNA fragments (=nucleic acids according to the invention) to one another adaptors or linkers may be attached to the fragments.

The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which encodes a Δ 6-desaturase gene and a region for transcription termination. Different termination regions can be exchanged for one another in any desired fashion.

Furthermore, manipulations which provide suitable restriction interfaces or which remove excess DNA or restriction interfaces can be employed. Where insertions, deletions or substitutions, such as transitions and transversions, come into consideration, in vitro mutagenesis, primer repair, restriction or ligation may be used. In suitable manipulations such as restriction, chewing back or filling of overhangs for blunt ends complementary ends of the fragments can be provided for the ligation.

For an advantageous high expression the attachment of the specific ER retention signal SEKDEL inter alia can be of importance (Schouten, A. et al., Plant Mol. Biol. 30 (1996), 781-792). In this way the average expression level is tripled or even quadrupled. Other retention signals which occur naturally in plant and animal proteins located in the ER may also be employed for the construction of the cassette.

Preferred polyadenylation signals are plant polyadenylation signals, preferably those which substantially correspond to T-DNA polyadenylation signals from *Agrobacterium tumefaciens*, in particular gene 3 of the T-DNA (octopin synthase) of the Ti plasmid pTiACH5 (Gielen et al., EMBO J. 3 (1984), 835 et seq.) or corresponding functional equivalents.

An expression cassette is produced by fusion of a suitable promoter with a suitable Δ 6-desaturase DNA sequence together with a polyadenylation signal by common recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

In the preparation of an expression cassette various DNA fragments can be manipulated to produce a nucleotide sequence which usefully reads in the correct direction and is equipped with a correct reading raster. Adapters or linkers can be attached to the fragments for joining the DNA fragments.

The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which encodes a Δ 6-desaturase gene and a region for transcription termination. Different termination regions can be exchanged for one another in any desired fashion.

In the preparation of an expression cassette various DNA fragments can be manipulated to produce a nucleotide sequence which usefully reads in the correct direction and is equipped with a correct reading raster. Adapters or linkers can be attached to the fragments for joining the DNA fragments.

The DNA sequences encoding two Δ 6-desaturases from *Muscariodides vialii* and *Aleuritia farinosa* contain all the sequence characteristics needed to achieve correct localization of the site of fatty acid, lipid or oil biosynthesis. Accordingly, no further targeting sequences are needed per se. However, such a localization may be desirable and advantageous and hence artificially modified or reinforced so that such fusion constructs are also a preferred advantageous embodiment of the invention.

Particularly preferred are sequences which ensure targeting in plastids. Under certain circumstances targeting into other compartments (reported in: Kermode, Crit. Rev. Plant Sci. 15, 4 (1996), 285-423) may also be desirable, e.g. into vacuoles, the mitochondrium, the endoplasmic reticulum (ER), peroxisomes, lipid structures or due to lack of corresponding operative sequences retention in the compartment of origin, the cytosol.

Advantageously, the nucleic acid sequences according to the invention or the gene construct together with at least one reporter gene are cloned into an expression cassette which is introduced into the organism via a vector or directly into the genome. This reporter gene should allow easy detection via a growth, fluorescence, chemical, bioluminescence or resistance assay or via a photometric measurement. Examples of reporter genes which may be mentioned are antibiotic- or herbicide-resistance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxy-glucose-6-phosphate phosphatase gene, the β-glucuronidase gene, β-lactamase gene, the neomycin phosphotransferase gene, the hygromycin phosphotransferase gene or the BASTA (=gluphosinate-resistance) gene. These genes permit easy measurement and quantification of the transcription activity and hence of the expression of the genes. In this way genome positions may be identified which exhibit differing productivity.

In a preferred embodiment an expression cassette comprises upstream, i.e. at the 5' end of the encoding sequence, a promoter and downstream, i.e. at the 3' end, a polyadenylation signal and optionally other regulatory elements which are operably linked to the intervening encoding sequence for Δ 6-desaturase and/or Δ 6-desaturase DNA sequence. By an operable linkage is meant the sequential arrangement of promoter, encoding sequence, terminator and optionally other regulatory elements in such a way that each of the regulatory elements can fulfill its function in the expression of the encoding sequence in due manner. The sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 (1987), 8693-8711).

An expression cassette may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a prokaryotic or eukaryotic host organism, for example a microorganism such as a fungus or a plant the expression cassette is advantageously inserted into a vector such as by way of example a plasmid, a phage or other DNA which allows optimum expression of the genes in the host organism. Examples of suitable plasmids are: in *E. coli* pLG338, pACYC184, pBR series such as e.g. pBR322, pUC series such as pUC18 or pUC19, M113 mp series, pKC30, pRep4, pHS1, pHS2, pPLc236, pMBL24, pLG200, pUR290, pIN-III[113]-B1, λgt11 or pBdCI; in *Streptomyces* pIJ101, pIJ364, pIJ702 or pIJ361; in *Bacillus* pUB110, pC194 or pBD214; in *Corynebacterium* pSA77 or pAJ667; in fungi pALS1, pIL2 or pBB116; other advantageous fungal vectors are described by Romanos, M. A. et al., [(1992) "Foreign gene expression in yeast: a review", *Yeast* 8: 423-488] and by van den Hondel, C. A. M. J. J. et al. [(1991) "Heterologous gene expression in filamentous fungi" as well as in More Gene Manipulations in Fungi [J. W. Bennet & L. L. Lasure, eds., pp. 396-428: Academic Press: San Diego] and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2∝M, pAG-1, YEp6, YEp13 or pEMB-LYe23. Examples of algal or plant promoters are pLGV23, pGHlac+, pBIN19, pAK2004, PVKH or pDH51 (see Schmidt, R. and Willmitzer, L., 1988). The vectors identified above or derivatives of the vectors identified above are a small selection of the possible plasmids. Further plasmids are well known to those skilled in the art and may be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), Ch. 6/7, pp. 71-119. Advantageous vectors are known as shuttle vectors or binary vectors which replicate in *E. coli* and *Agrobacterium*.

By vectors is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

In a further advantageous embodiment the nucleic acid sequence according to the invention can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

By way of example the plant expression cassette can be installed in the pRT transformation vector ((a) Toepfer et al., 1993, Methods Enzymol., 217: 66-78; (b) Toepfer et al. 1987, Nucl. Acids. Res. 15: 5890 ff.).

Alternatively, a recombinant vector (=expression vector) can also be transcribed and translated in vitro, e.g. by using the T7 promoter and the T7 RNA polymerase.

Expression vectors employed in prokaryotes frequently make use of inducible systems with and without fusion proteins or fusion oligopeptides, wherein these fusions can ensue in both N-terminal and C-terminal manner or in other useful domains of a protein. Such fusion vectors usually have the following purposes: i.) to increase the RNA expression rate; ii.) to increase the achievable protein synthesis rate; iii.) to increase the solubility of the protein; iv.) or to simplify purification by means of a binding sequence usable for affinity chromatography. Proteolytic cleavage points are also frequently introduced via fusion proteins which allows cleavage of a portion of the fusion protein and purification. Such recognition sequences for proteases are recognized, e.g. factor Xa, thrombin and enterokinase.

Typical advantageous fusion and expression vectors are pGEX [Pharmacia Biotech Inc; Smith, D. B. and Johnson, K. S. (1988) *Gene* 67: 31-40], pMAL (New England Biolabs, Beverly, Mass.) and pRIT5 (Pharmacia, Piscataway, N.J.) which contains glutathione S-transferase (GST), maltose binding protein or protein A.

Other examples of *E. coli* expression vectors are pTrc [Amann et al., (1988) Gene 69:301-315] and pET vectors [Studier et al., Gene Expression Technology: Methods in Enzymology 185, Academic Press, San Diego, Calif. (1990) 60-89; Stratagene, Amsterdam, The Netherlands].

Other advantageous vectors for use in yeast are pYepSec1 (Baldari, et al., (1987) *Embo J.* 6:229-234), pMFa (Kurian and Herskowitz, (1982) *Cell* 30:933-943), pJRY88 (Schultz et al., (1987) *Gene* 54:113-123), and pYES derivatives (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi", in: Applied Molecular Genetics of Fungi, J. F. Peberdy, et al., eds., pp. 1-28, Cambridge University Press: Cambridge.

Alternatively, insect cell expression vectors can also be advantageously utilized, e.g. for expression in Sf 9 cells. These are e.g. the vectors of the pAc series (Smith et al. (1983) *Mol. Cell Biol.* 3:2156-2165) and the pVL series (Lucklow and Summers (1989) *Virology* 170:31-39).

Furthermore, plant cells or algal cells can advantageously be used for gene expression. Examples of plant expression vectors may be found in Becker, D., et al. (1992) "New plant binary vectors with selectable markers located proximal to the left border", *Plant Mol. Biol.* 20: 1195-1197 or in Bevan, M. W. (1984) "Binary *Agrobacterium* vectors for plant transformation", *Nucl. Acid. Res.* 12: 8711-8721.

Furthermore, the nucleic acid sequences according to the invention may be expressed in mammalian cells, advantageously in nonhuman mammalian cells. Examples of corresponding expression vectors are pCDM8 and pMT2PC referred to in: Seed, B. (1987) *Nature* 329:840 or Kaufman et al. (1987) *EMBO J.* 6: 187-195). At the same time promoters preferred for use are of viral origin, such as by way of example promoters of polyoma, adenovirus 2, cytomegalovirus or simian virus 40. Other prokaryotic and eukaryotic expression systems are referred to in chapters 16 and 17 of Sambrook et al., *Molecular Cloning: A Laboratory Manual. 2nd, ed., Cold Spring Harbor Laboratory*, Cold Spring Harbor Laboratory Press, Cold Spring Harbor, N.Y., 1989.

The introduction of the nucleic acids according to the invention, the expression cassette or the vector into organisms, plants for example, can in principle be done by all of the methods known to those skilled in the art. The introduction of the nucleic acid sequences gives rise to recombinant or transgenic organisms.

In the case of microorganisms, those skilled in the art can find appropriate methods in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The construct to be expressed is preferably cloned into a vector which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

*Agrobacteria* transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassaya, arrowroot, tagetes, alfalfa, lettuce and the various tree, nut and vine species, in particular of oil-containing crop plants such as soybean, peanut, castor oil plant, sunflower, corn, cotton, flax, oilseed rape, coconut, oil palm, safflower (*Carthamus tinctorius*) or cocoa bean, e.g. by bathing bruised leaves or chopped leaves in an agrobacterial solution and then culturing them in suitable media. For the production of PUFAs, for example stearidonic acid, eicosapentaenoic acid and docosahexaenoic acid, borage or Primulaceae are advantageously suitable.

The genetically modified plant cells may be regenerated by all of the methods known to those skilled in the art. Appropriate methods can be found in the publications referred to above by S. D. Kung and R. Wu, Potrykus or Höfgen and Willmitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms—or reproductive material derived from such organisms. The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

For the purposes of the invention "transgenic" or "recombinant" means with regard for example to a nucleic acid sequence, an expression cassette (=gene construct) or a vector containing the nucleic acid sequence according to the invention or an organism transformed by the nucleic acid sequences, expression cassette or vector according to the invention all those constructions produced by genetic engineering methods in which either a) the nucleic acid sequence according to the invention or b) a genetic control sequence functionally linked to the nucleic acid sequence according to the invention, for example a promoter, or c) (a) and (b)

are not found in their natural, genetic environment or have been modified by genetic engineering methods, wherein the modification may by way of example be a substitution, addition, deletion, inversion or insertion of one or more nucleotide residues. Natural genetic environment means the natural genomic or chromosomal locus in the organism of origin or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette—for example the naturally occurring combination of the natural promoter of the nucleic acid sequence according to the invention with the corresponding PSE gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815.

Suitable organisms or host organisms for the nucleic acid, expression cassette or vector according to the invention are advantageously in principle all organisms which are able to synthesize fatty acids, especially unsaturated fatty acids or are suitable for the expression of recombinant genes. Examples which may be mentioned are plants such as *Arabidopsis*, Asteraceae such as *Calendula* or crop plants such as soybean, peanut, castor oil plant, sunflower, corn, cotton, flax, oilseed rape, coconut, oil palm, safflower (*Carthamus tinctorius*) or cocoa bean, microorganisms such as fungi, for example the genus *Mortierella, Sapro-legnia* or *Pythium*, bacteria such as the genus *Escherichia*, yeasts such as the genus *Saccharomyces*, cyanobacteria, ciliates, algae or protozoa such as dinoflagellates like *Crypthecodinium*. Preference is given to organisms which can naturally synthesize oils in relatively large quantities such as fungi like *Mortierella alpina, Pythium insidiosum* or plants such as soybean, oilseed rape, coconut, oil palm, safflower, flax, castor oil plant, *Calendula*, peanut, cocoa bean or sunflower, or yeasts such as *Saccharomyces cerevisiae* and particular preference is given to soybean, flax, oilseed rape, sunflower, *Calendula, Mortierella* or *Saccharomyces cerevisiae*. In principle, apart from the transgenic organisms identified above, transgenic animals, advantageously nonhuman animals, are suitable, for example *C. elegans*.

Further useful host cells are identified in: Goeddel, *Gene Expression Technology: Methods in Enzymology* 185, Academic Press, San Diego, Calif. (1990).

Usable expression strains, e.g. those exhibiting a relatively low protease activity, are described in: Gottesman, S., *Gene Expression Technology: Methods in Enzymology* 185, Academic Press, San Diego, Calif. (1990) 119-128.

A further object of the invention relates to the use of an expression cassette containing DNA sequences encoding a Δ 6-desaturase gene or DNA sequences hybridizing therewith for the transformation of plant cells, tissues or parts of plants. The aim of use is to increase the content of fatty acids, oils or lipids having an increased content of double bonds in the Δ 6 position.

In doing so, depending on the choice of promoter, the Δ 6-desaturase gene can be expressed specifically in the leaves, in the seeds, the nodules, in roots, in the stem or other parts of the plant. Those transgenic plants overproducing fatty acids, oils or lipids having Δ 6 double bonds, the reproductive material thereof, together with the plant cells, tissues or parts thereof are a further object of the present invention. A preferred object according to the invention comprises transgenic plants containing a functional or nonfunctional (=antisense DNA or enzymatically inactive enzyme) nucleic acid sequence or a functional or nonfunctional expression cassette according to the invention.

The expression cassette or the nucleic acid sequences according to the invention containing a Δ 6-desaturase gene sequence can, moreover, also be employed for the transformation of the organisms identified by way of example above such as bacteria, cyanobacteria, yeasts, filamentous fungi, ciliates and algae with the objective of increasing the content of fatty acids, oils or lipids possessing Δ 6 double bonds.

Within the framework of the present invention, increasing the content of fatty acids, oils or lipids possessing Δ 6 double bonds means, for example, the artificially acquired trait of increased biosynthetic performance due to functional overexpression of the Δ 6-desaturase gene in the organisms according to the invention, advantageously in the transgenic plants according to the invention, by comparison with the nongenetically modified initial plants at least for the duration of at least one plant generation.

The preferred locus of biosynthesis, of fatty acids, oils or lipids for example, is generally the seed or cell layers of the seed so that a seed-specific expression of the Δ 6-desaturase gene is appropriate. It is, however, obvious that the biosynthesis of fatty acids, oils or lipids need not be limited to the seed tissue but rather can also occur in tissue-specific manner in all other parts of the plant—in epidermis cells or in the nodules for example.

A constitutive expression of the exogenous Δ 6-desaturase gene is, moreover, advantageous. On the other hand, however, an inducible expression may also appear desirable.

The efficiency of the expression of the Δ 6-desaturase gene can be determined, for example, in vitro by shoot meristem propagation. In addition, an expression of the Δ 6-desaturase gene modified in nature and level and its effect on fatty acid, oil or lipid biosynthesis performance can be tested on test plants in greenhouse trials.

An additional object of the invention comprises transgenic organisms such as transgenic plants transformed by an expression cassette containing a Δ 6-desaturase gene sequence according to the invention or DNA sequences hybridizing therewith, as well as transgenic cells, tissue, parts and reproduction material of such plants. Particular preference is given in this case to transgenic crop plants such as by way of example barley, wheat, rye, oats, corn, soybean, rice, cotton, sugar beet, oilseed rape and canola, sunflower, flax, hemp, thistle, potatoes, tobacco, tomatoes, oilseed rape, tapioca, cassava, arrowroot, alfalfa, lettuce and the various tree, nut and vine species.

For the purposes of the invention plants are mono- and dikotylodonous plants, mosses or algae.

A further refinement according to the invention are transgenic plants as described above which contain a functional or nonfunctional nucleic acid sequence according to the invention or a functional or nonfunctional expression cassette according to the invention. By nonfunctional is meant that an enzymatically active protein is no longer synthesized. Moreover, by nonfunctional nucleic acids or nucleic acid constructs is also means what is known as an antisense DNA which results in transgenic plants which show a reduction in enzymatic activity or no enzymatic activity. With the aid of the antisense technique, especially when the nucleic acid sequence is combined in the antisense DNA with other fatty acid synthesis genes, it is possible to synthesize triglycerides having an increased content of saturated fatty acids or saturated fatty acids. Furthermore, by means of what is known as coexpression or by means of the RNAi technique transgenic plants can be manipulated in such a way that no or reduced enzymatic activity is produced in the plants. By transgenic plants is meant single plant cells and cultures thereof on fixedmedia or in liquid culture, parts of plants and entire plants.

Other objects of the invention are:

A method for the transformation of a plant comprising the introduction of expression cassettes according to the invention containing a Δ 6-desaturase gene sequence derived from Primulaceae or DNA' sequences hybridizing therewith into a plant cell, into callus tissue, an entire plant or protoplasts of plants.

A method for producing PUFAs, wherein the method comprises the growing of a transgenic organism comprising a nucleic acid as claimed in claims 1 to 4, a gene construct as claimed in claim 6 or a vector as claimed in claim 7 encoding a Δ 6-desaturase which specifically desaturates ω-3 fatty acids, and wherein due to the activity of the Δ 6-desaturase PUFAs are formed in the organism which exhibit an increased content of ω-3 fatty acids. In this method ω-3 fatty acids such as stearidonic acid, eicosapentaenoic acid or docosahexaenoic acid are advantageously produced.

Use of a Δ 6-desaturase DNA gene sequence or DNA sequences hybridizing therewith for the production of plants having an increased content of fatty acids, oils or lipids having Δ 6 double bonds due to the expression of said Δ 6-desaturase DNA sequence in plants.

Use of a Δ 6-desaturase DNA gene sequence DNA sequences hybridizing therewith for the production of plants having an increased content of fatty acids, oils or lipids having Δ 6 double bonds, particularly of ω-3 fatty acids, due to the expression of said Δ 6-desaturase DNA sequence in plants.

Proteins containing the amino acid sequences depicted in SEQ ID NO: 2 or NO: 4.

Use of said proteins having the sequences SEQ ID NO: 2 or NO: 4 for producing unsaturated fatty acids.

A further object according to the invention is a method for producing unsaturated fatty acids comprising: introducing at least one said nucleic acid sequence according to the invention or at least one nucleic acid construct according to the invention into a preferably oil-producing plant; growing said organism; isolating oil contained in said organism; and liberating the fatty acids present in said oil. These unsaturated fatty acids advantageously contain Δ 6 double bonds. The fatty acids may be liberated from the oils or lipids, for example by basic hydrolysis, e.g. using NaOH or KOH.

A method for producing triglycerides having an increased content of unsaturated fatty acids comprising: introducing at least one said nucleic acid sequence according to the invention or at least one expression cassette according to the invention into an oil-producing organism; growing said organism; and isolating oil contained in said organism; is also numbered among the objects of the invention.

A further object according to the invention is a method for producing triglycerides having an increased content of unsaturated fatty acids by incubating triglycerides containing saturated or unsaturated or saturated and unsaturated fatty acids with at least one of the proteins encoded by the sequences SEQ ID NO: 2 or NO: 4. The method is advantageously carried out in the presence of compounds which can take up or release reduction equivalents. The fatty acids can then be liberated from the triglycerides.

A further object according to the invention of said method for producing triglycerides having an increased content of saturated or unsaturated fatty acids or saturated and unsaturated fatty acids advantageously having an increased content of unsaturated fatty acids is a method wherein the fatty acids are liberated from the triglycerides with the aid of basic hydrolysis known to those skilled in the art or by means of an enzyme such as a lipase.

The methods specified above advantageously allow the synthesis of fatty acids or triglycerides having an increased content of fatty acids containing Δ 6 double bonds.

The methods identified above advantageously allow the synthesis of fatty acids or triglycerides having an increased content of fatty acids containing Δ 6 double bonds, wherein the substrate used for the reaction of the Δ 6-desaturase is preferably α-linolenic acid. In this way the method identified above advantageously allows in particular the synthesis of fatty acids derived from stearidonic acid ($C_{18:4}^{\Delta 6, 9, 12, 15}$) such as by way of example eicosapentaenoic acid and docosahexaenoic acid.

Using what is known as antisense technology, in one method fatty acids or triglycerides having an increased content of saturated fatty acids can also be produced.

Examples of organisms for the said methods which may be mentioned are plants such as *Arabidopsis*, Primulaceae, borage, barley, wheat, rye, oats, corn, soybean, rise, cotton, sugar beet, oilseed rape and canola, sunflower, flax, hemp, potatoes, tobacco, tomatoes, rape, tapioca, cassaya, arrowroot, alfalfa, peanut, castor oil plant, coconut, oil palm, safflower (*Carthamus* tinctorius) or cocoa bean, microorganisms such as the fungi *Mortierella*, *Saprolegnia* or *Pythium*, bacteria such as the genus *Escherichia*, cyanobacteria, yeasts such as the genus *Saccharomyces*, algae or protozoa such as dinoflagellates like *Crypthecodinium*. Preference is given to organisms which can naturally synthesize oils in relatively large quantities such as fungi like *Mortierella alpina*, *Pythium insidiosum* or plants such as soybean, oilseed rape, coconut, oil palm, safflower, castor oil plant, *Calendula*, peanut, cocoa bean or sunflower, or yeasts such as *Saccharomyces cerevisiae* and particular preference is given to soybean, oilseed rape, sunflower, flax, Primulaceae, borage, *Carthamus* or *Saccharomyces cerevisiae*.

Depending on the host organism, the organisms used in the methods are grown or cultured in the manner known to those skilled in the art. Microorganisms are usually grown in a liquid medium containing a carbon source, usually in the form of sugars, a nitrogen source, usually in the form of organic nitrogen sources such as yeast extract or salts such as ammonium sulfate, trace elements such as iron, manganese or magnesium salts and optionally vitamins at temperatures of between 10° C. and 60° C. with exposure to gaseous oxygen. In doing so the pH of the nutrient liquid may be kept at a fixed value, that is during growth it is or is not regulated. Growth can ensue in batch mode, semibatch mode or continuously. Nutrients can be provided at the start of fermentation or be fed in semicontinuously or continuously.

After transformation plants are first of all regenerated as described above and then cultured or cultivated as normal.

After growth the lipids are isolated from the organisms in the usual way. For this purpose, after harvesting the organisms may first of all be digested or used directly. The lipids are advantageously extracted using suitable solvents such as apolar solvents like hexane or ethanol, isopropanol or mixtures such as hexane/isopropanol, phenol/chloroform/isoamyl alcohol at temperatures of between 0° C. and 80° C., preferably between 20° C. and 50° C. The biomass is usually extracted with an excess of solvent, for example an excess of solvent to biomass of 1:4. The solvent is then removed, for example by distillation. Extraction can also be done using supercritical $CO_2$. After extraction the remaining biomass may be removed, for example by filtration.

The crude oil isolated in this way can then be further purified, for example by removing cloudiness by treatment with polar solvents such as acetone or chloroform and then filtration or centrifugation. Further purification through columns is also possible.

In order to obtain the free acids from the triglycerides the latter are saponified in the usual way.

A further object of the invention comprises unsaturated fatty acids and triglycerides having an increased content of unsaturated fatty acids produced by the methods identified above and use thereof for producing foods, animal feeds, cosmetics or pharmaceuticals. For this purpose the latter are added in customary quantities to the foods, the animal feed, the cosmetics or pharmaceuticals.

Said unsaturated fatty acids according to the invention as well as triglycerides having an increased content of unsaturated fatty acids produced by the methods identified above are the result of the expression of the nucleic acids according to the invention in the various host organisms. This results overall in a modification of the composition of the compounds in the host cell containing unsaturated fatty acids by comparison with the original starting host cells which do not contain the nucleic acids. These modifications are more marked in host organisms, for example plant cells, which naturally do not contain the proteins or enzymes encoded by the nucleic acids than in host organisms which naturally do contain the proteins or enzymes encoded by the nucleic acids. This gives rise to host organisms containing oils, lipids, phospholipids, sphingolipids, glycolipids, triacylglycerols and/or free fatty acids having a higher content of PUFAs. For the purposes of the invention, by an increased content is meant that the host organisms contain at least 5%, advantageously at least 10%, preferably at least 20%, particularly preferably at least 30%, most particularly preferably at least 40% more polyunsaturated fatty acids by comparison with the initial organism which does not contain the nucleic acids according to the invention. This is particularly the case for plants which do not naturally contain longer-chain polyunsaturated $C_{20}$ or $C_{22}$ fatty acids such as DHA, EPA or ARA. Due to the expression of the nucleic acids novel lipid compositions are produced by said means these being a further aspect of the invention.

The invention is explained in more detail by the following examples.

Further, the following examples illustrate embodiments of the invention, but should not be viewed as limiting the scope of the invention.

EXAMPLES

Example 1

General Cloning Methods

The cloning methods, such as by way of example restriction cleavages, agarose gel electrophoresis, purification of DNA fragments, transfer of nucleic acids to nitrocellulose and nylon membranes, linkage of DNA fragments, transformation of *Escherichia coli* cells, culture of bacteria and sequence analysis of recombinant DNA, were carried out as described in Sambrook et al. (1989) (Cold Spring Harbor Laboratory Press: ISBN 0-87969-309-6).

Example 2

Sequence Analysis of Recombinant DNA

Sequencing of recombinant DNA molecules was done using a laser fluorescence DNA sequencer from the ABI company by the method of Sanger (Sanger et al. (1977) Proc. Natl. Acad. Sci. USA74, 5463-5467). Fragments resulting from a polymerase chain reaction were sequenced and checked to prevent polymerase errors in the constructs to be expressed.

Example 3

Cloning of the Δ 6-Desaturase from *Muscariodides vialii* (=SEQ ID NO: 3)

Total RNA from young *Muscariodides vialii* leaves was isolated with the aid of the RNAeasy kit from the Qiagen company (Valencia, Calif., USA). With the aid of oligo-dT-cellulose poly-A+RNA (mRNA) was isolated from the total RNA (Sambrook et al., 1989). Using the Reverse Transcription System kit from Promega the RNA was reverse transcribed and the synthesized cDNA was used for PCR amplification of the Δ 6-desaturases. Degenerate primers were used for the amplification of the Δ 6-desaturase. The nucleotide sequence was derived from the first and the third histidine box motif of borage Δ 6-desaturase (Syanova et al., 1997, WO9621022).

```
                                      (SEQ ID NO: 5)
     Primer 1: GGITGGHTIGGICAYGAYKYIKSICA (SEQ ID NO: 6)
     Primer 2: GGRAAIAGRTGRTGYTCDATYTG
```

In the primers identified here and in the primer sequences set out below the symbols or letters in accordance with Wobble IUPAC-IUB have the following meaning:

R=A/G; Y=C/T; M=A/C; K G/T; S=G/C; W=A/T; H=A/C/T; B=G/T/C; V=G/C/A; D=G/T/A und N=G/A/T/C.

PCR Protocol
Addition temperature: 1 min at 45° C.
Denaturing temperature: 1 min at 94° C.
Elongation temperature: 2 min at 72° C.
Number of cycles: 35

The PCR mixture was separated on an agarose gel and a 660 bp fragment was isolated. The PCR fragment was cloned in the pGEM-T easy vector (Promega) and the insert was then sequenced.

The missing 5' and 3' region of the isolated gene fragment from *Muscariodides vialii* was isolated with the aid of the Smart RACE cDNA kit (Clonetech) and then sequenced. Starting from 3' and 5' sequence primers were derived in order to isolate the complete clone. For this purpose primers were derived from the DNA regions around the start methionine and the stop codon. The PCR yielded a single band of the expected size. The cDNA was again cloned in the pGEM T easy vector and the now complete gene was sequenced.

Example 4

Cloning of the Δ 6-Desaturase from *Aleuritia farinosa* (=SEQ ID NO: 1)

Total RNA from young *Aleuritia farinose* leaves was isolated with the aid of the RNAeasy kit from the Qiagen company (Valencia, Calif., USA). With the aid of oligo-dT-cellulose poly-A+ RNA (mRNA) was isolated from the total RNA (Sambrook et al., 1989). Using the Reverse Transcription System kit from Promega the RNA was reverse transcribed and the synthesized cDNA was used for PCR amplification of the Δ 6-desaturases. Degenerate primers were used for the amplification of the Δ 6-desaturase. The nucleotide sequence was derived from the first and the third histidine box motif of borage Δ 6-desaturase (Syanova et al., 1997, WO9621022)

```
                                          (SEQ ID NO: 5)
    Primer 1:  GGITGGHTIGGICAYGAYKYIKSICA (SEQ ID NO: 6)
    Primer 2:  GGRAAIAGRTGRTGYTCDATYTG
```

PCR Protocol
Addition temperature: 1 min at 45° C.
Denaturing temperature: 1 min at 94° C.
Elongation temperature: 2 min at 72° C.
Number of cycles: 35

The PCR mixture was separated on an agarose gel and a 660 bp fragment was isolated. The PCR fragment was cloned in the pGEM-T easy vector (Promega) and the insert was then sequenced.

The missing 5' and 3' region of the isolated gene fragment from *Aleuritia farinose* was isolated with the aid of the Smart RACE cDNA kit (Clonetech) and then sequenced. Starting from 3' and 5' sequence primers were derived in order to isolate the complete clone. For this purpose primers were derived from the DNA regions around the start methionine and the stop codon. The PCR yielded a single band of the expected size. The cDNA was again cloned in the pGEM T easy vector and the now complete gene was sequenced.

Example 5

Cloning of Expression Plasmids for Constitutive Expression in Plants

By means of appropriate primers at the 5' and 3' end of both new desaturases a CLAI and a XbaI interface was introduced.
Primer design for the Δ 6-desaturase from *M. vialli*:

```
                                                (SEQ ID NO: 7)
    atcgatatggctaacaaatctcccacc    (ClaI)

(SEQ ID NO: 8)
    tctagattagccgtgtgtgtggacggctt  (XbaI)
```

Primer design for the Δ 6-desaturase from *A. farinosa*:

```
                                                (SEQ ID NO: 7)
    atcgatatggctaacaaatctcccacc    (claI)

(SEQ ID NO: 9)
    tctagatcacccgagagttttaagagct   (XbaI)
```

The PCR products were separated in agarose gel, digested with ClaI/XbaI and ligated into the appropriately cut vector pSLJ4K1. The resultant plasmids contain 35S promoter (cauliflower mosaic virus; Franck et al. (1980) Cell 21, 285), the Δ 6-desaturase from *Muscariodides vialii* or *Aleuritia farinosa* and the 35S terminator in the vector pSLJ4K1. Apart from said promoters or terminators all constitutive promoters or all plant virus promoters such as advantageously the nos promoter (Wilkinson et al., Journal of Experimental Botany, 48, 1997: 307 et seq.) or the ubiquintin promoter may be used. The promoters and terminators identified in the description may also advantageously be used in principle for expression.

The constructs were used for the transformation of *Arabidopsis thaliana*, oilseed rape, tobacco and linseed.

Example 5

Cloning of Expression Plasmids for Seed-specific Expression in Plants

For the transformation of plants a further transformation vector based on pBin-USP containing the BamHI fragments of the Δ 6-desaturases from *M. vialii* or *A. farinosa* was produced. The BamHI interfaces were, as described in Example 4 [5? This is the second Example 5!], attached to the start ATGs or stop codons with the aid of appropriate primers by PCR.

Primer design for the Δ 6-desaturase from *M. vialii*:

```
                                               (SEQ ID NO: 10)
        ggatccatggctaacaaatctcccacc (SEQ ID NO: 11)
        ggatccttagccgtgtgtgtggacggctt
```

Primer design for the Δ 6-desaturase from *A. farinosa*:

```
                                               (SEQ ID NO: 10)
        ggatccatggctaacaaatctcccacc (SEQ ID NO: 12)
        ggatcctcacccgagagttttaagagct
``` pBin-USP is a derivative of the plasmid pBin19. pBin-USP was produced from pBin19 by inserting a USP promoter as an EcoRI-BaMHI fragment into pBin19 (Bevan et al. (1980) Nucl. Acids Res. 12, 8711). The polyadenylation signal is that of gene 3 of the T-DNA of the Ti plasmid pTiACH5 (Gielen et al., (1984) EMBO J. 3, 835), whereby nucleotides 11749-11939 were isolated as a PvuII-HindIII fragment and after addition of SphI linkers to the PvuII interface between the SpHI-HindIII interface of the vector were cloned. The USP promoter corresponds to nucleotides 1-684 (gene bank accession number X56240), wherein a part of the nonencoding region of the USP gene is contained in the promoter. The promoter fragment running to 684 base pairs was amplified by standard methods by means of commercial T7 standard primer (Stratagene) and using a synthesized primer through a PCR reaction. (Primer sequence: 5'-GTCGACCCGCGGAC-TAGTGGGCCCTCTAGACCCGGGGGATCC GGATCT-GCTGGCTATGAA-3' (SEQ ID NO: 13)). The PCR fragment was recut using EcoRI/SalI and inserted into the vector pBin19 with OCS terminator. The plasmid having the designation pBinUSP was obtained. The constructs were used for transforming *Arabidopsis thaliana*, oilseed rape, tobacco and linseed.

Example 6

Production of Transgenic Plants a) Production of transgenic plants (modified in accordance with Moloney et al., 1992, Plant Cell Reports, 8:238-242)
To produce transgenic oilseed rape plants binary vectors in *Agrobacterium tumefaciens* C58C1:pGV2260 or *Escherichia coli* were used (Deblaere et al, 1984, Nucl. Acids. Res. 13, 4777-4788). For transforming oilseed rape plants (var. *Drakkar*, NPZ Nordeutsche Pflanzenzucht, Hohenlieth, Germany) a 1:50 dilution of an overnight culture of a positively transformed agrobacteria colony in Murashige-Skoog medium (Murashige and Skoog 1962 Physiol. Plant. 15, 473) containing 3% of saccharose (3MS medium) was used. Petioles or hypocotyledons of freshly germinated sterile rape plants (approx. 1 cm² each) were incubated in a Petri dish with a 1:50 agrobacteria dilution for 5-10 minutes. This was followed by 3-day concubation in darkness at 25° C. on 3MS medium containing 0.8% of Bacto-Agar. After three days, culturing was continued with 16 hours of light/8 hours of darkness and in a weekly cycle on MS medium containing 500 mg/l of Claforan (sodium cefotaxime), 50 mg/l of kanamycin, 20 microM of benzy-laminopurine (BAP) and 1.6 g/l of glucose. Growing shoots were transferred onto MS medium containing 2% of saccharose, 250 mg/l of Claforan and 0.8% of Bacto-Agar. If after three weeks no roots had formed 2-indolylbutyric acid was added to the medium as a growth hormone for rooting purposes.

Regenerated shoots were obtained on 2MS medium using kanamycin and Claforan, transferred into soil after rooting and after culturing grown for two weeks in a climate-controlled chamber, brought to blossom and after harvesting of ripe seed investigated for Δ 6-desaturase expression by means of lipid analyses. Lines having increased contents of double bonds at the Δ 6 position were identified. In the stably transformed transgenic lines functionally expressing the transgene it was found that there is an increased content of double bonds at the Δ 6 position by comparison with untransformed control plants.

b) Transgenic flax plants may be produced, for example by the by the method bell et al., 1999, In Vitro Cell. Dev. Biol.-Plant. 35(6):456-465, by means of particle bombardment. Agrobacteria-mediated transformations can be produced, for example, as described by Mlynarova et al. (1994), Plant Cell Report 13: 282-285.

Example 7

Lipid Extraction from Seed

Plant material was first of all mechanically homogenized by means of triturators in order to render it more amenable to extraction.

It was then heated to 100° C. for 10 min and after cooling on ice sedimented again. The cell sediment was hydrolyzed with 1 M methanolic sulfuric acid and 2% dimethoxypropane for 1 h at 90° C. and the lipids were transmethylated. The resultant fatty acid methyl esters (FAMEs) were finally extracted into petroleum ether. The extracted FAMEs were analyzed by gas-liquid chromatograph using a capillary column (Chrompack, WCOT fused silica, CP wax 52 CB, 25 m, 0.32 mm) and a temperature gradient of from 170° C. to 240° C. in 20 min and 5 min at 240° C. The identity of the fatty acid methyl esters was confirmed by comparison with corresponding FAME standards (Sigma). The identity and the position of the double bond was further analyzed by means of GC-MS by suitable chemical derivatization of the FAME mixtures, e.g. to form 4,4-dimethoxyoxazoline derivatives (Christie, 1998). The GC analyses of the fatty acid methyl esters obtained from the transgenic rape seeds exhibiting seed-specific expression of the Δ 6-desaturase are presented in Table 1. The transgenic rape seeds contained up to 5% of γ-linolenic acid in the seed.

Example 8

Expression of Δ 6-desaturases from Primulaceae in Yeast (*Saccharomyces cerevisiae*)

The open reading rasters of the Δ 6-desaturases obtained from *Muscariodides vialii* and *Aleuritia farinosa* were each cloned behind the galactose-inducible GAL1 promoter of the yeast expression vector pYES2 (Invitrogen). The open reading rasters were amplified by means of PCR. The interfaces used for cloning were KpnI and EcoRI.

Primer design for *M. vialii*:

```
                                          (SEQ ID NO: 14)
    ggtaccatggctaacaaatctcccacc    (KpnI)

(SEQ ID NO: 15)
    gaattcttagccgtgtgtgtggacggctt  (EcoRI)
```

Primer design for *A. farinosa*:

```
                                          (SEQ ID NO: 14)
    ggtaccatggctaacaaatctcccacc    (KpnI)

(SEQ ID NO: 16)
    gaattctcacccgagagttttaagagct   (EcoRI)
```

The vectors produced were used for expression in yeast. The substrate specificities were determined by feeding the transformed yeast strains with α-linolenic acid and linoleic acid. The methodology used is described, for example, in Napier and Michaelson, 2001, Lipids. 36(8):761-766; Sayanova et al., 2001, Journal of Experimental Botany. 52(360): 1581-1585, Sperling et al., 2001, Arch. Biochem. Biophys. 388(2):293-298 and Michaelson et al., 1998, FEBS Letters. 439(3):215-218.

In order to compare the specificities the Δ 6-desaturase from borage (*Borago officinalis*) was likewise expressed in yeast (Sayanova et al., 1999, Plant Physiol. 121(2):641-646).

TABLE 1

Expression in yeast. Comparison of substrate specificities of Δ 6-desaturases from borage, *A. farinosa* (SEQ ID NO: 1) and *M. vialii*. (SEQ ID NO: 3).

| Fatty Acid | Construct pYES2 | Borage | A. farinosa | M. vialii |
|---|---|---|---|---|
| $C_{16:0}$ | 24.8 | 20 | 23.2 | 20.3 |
| $C_{16:1}^{\Delta 9}$ | 22.5 | 20 | 18.2 | 21.7 |
| $C_{18:0}$ | 6.1 | 6.2 | 5.9 | 4.7 |
| $C_{18:1}^{\Delta 9}$ | 17.1 | 17.1 | 14.9 | 15.8 |
| $C_{18:2}^{\Delta 9,12}$ | 13.8 | 11.5 | 12.8 | 15.3 |
| $C_{18:3}^{\Delta 6,9,12}$ | 0 | 5.5 | 5 | 1.4 |
| $C_{18:3}^{\Delta 9,12,15}$ | 15.6 | 15.5 | 12.2 | 13.9 |
| $C_{18:4}^{\Delta 6,9,12,15}$ | 0 | 3.9 | 7.7 | 6.8 |

TABLE 2

Conversion of linoleic acid by Δ 6-desaturase from borage and the Δ 6-desaturases from Primulaceae (*A. farinosa* (SEQ ID NO: 1) and *M. vialii* (SEQ ID NO:3)) by comparison with the conversion of α-linolenic acid.

| Construct | pYES2 | Borage | A. farinosa | M. vialii |
|---|---|---|---|---|
| % by wt. of Δ 6-desaturated fatty acids in the total fatty acids | nd | 11.10% | 14.10% | 8.80% |
| % conversion of LA to Δ 6 fatty acids | nd | 32.30% | 28.10% | 8.40% |
| % conversion of ALA to Δ 6 fatty acids | nd | 20.10% | 38.70% | 32.80% |
| Ratio n3:n6 | | 0.71 | 1.54 | 4.8 |

LA = linoleic acid (=$C_{18:2}^{\Delta 9,12}$) ⇒ Δ 6-desaturation produces $C_{18:3}^{\Delta 6,9,12}$
ALA = α-linolenic acid (=$C_{18:3}^{\Delta 9,12,15}$) ⇒ Δ 6-desaturation produces $C_{18:4}^{\Delta 6,9,12,15}$
nd = not determined It may be gathered from the tables that the nucleic acid sequences according to the invention encode Δ 6-desaturases which are specific for ω-3 fatty acids.

What is claimed is:

1. An isolated nucleic acid that encodes a polypeptide having Δ6-desaturase activity, wherein the polypeptide exhibits higher Δ6-desaturase activity for ω-3 fatty acids as compared to ω-6 fatty acids, wherein said nucleic acid is derived from a plant and wherein said nucleic acid comprises a nucleotide sequence selected from the group consisting of:
   a) the nucleotide sequence as set forth in SEQ ID NO: 1; and
   b) a nucleotide sequence that encodes a polypeptide comprising the amino acid sequence as set forth in SEQ ID NO: 2.

2. The isolated nucleic acid of claim 1, wherein said nucleic acid is derived from the genera *Muscariodides* or *Aleuritia*.

3. A gene construct containing the isolated nucleic acid of claim 1, wherein said nucleic acid is functionally linked to one or more regulation signals.

4. A vector containing the isolated nucleic acid of claim 1.

5. A transgenic nonhuman organism containing the isolated nucleic acid of claim 1, wherein the organism is a microorganism, yeast, or plant.

6. The transgenic nonhuman organism of claim 5, wherein said organism is a microorganism or a plant.

7. The transgenic nonhuman organism of claim 5, wherein said organism is a plant.

8. A method for producing polyunsaturated fatty acids, wherein the method comprises growing a transgenic organism which comprises the isolated nucleic acid of claim 1, wherein, due to the activity of said Δ-6 desaturase, polyunsaturated fatty acids are formed in said organism which exhibit an increased content of ω-3 fatty acids compared to a non-transformed organism, wherein the organism is a microorganism, yeast, or plant.

9. The method of claim 8, wherein stearidonic acid, eicosapentaenoic acid or docosahexaenoic acid is produced.

10. The method of claim 8, further comprising isolating polyunsaturated fatty acid molecules from said organism in the form of an oil, lipid or a free fatty acid.

11. The method of claim 8, wherein said organism is a microorganism or a plant.

12. The method of claim 8, wherein said organism is a transgenic plant.

13. The method of claim 10, wherein said polyunsaturated fatty acid molecules comprise a $C_{18}$ fatty acid having at least three double bonds.

14. The isolated nucleic acid of claim 1, wherein the Δ6-desaturase activity toward ω-3 fatty acids as compared to ω-6 fatty acids is higher by a factor of at least 1.5.

15. The isolated nucleic acid of claim 14, wherein the factor is at least 3.

16. The isolated nucleic acid of claim 14, wherein the factor is at least 5.

17. A vector containing the gene construct of claim 3.

18. A trangenic nonhuman organism containing the gene construct of claim 3, wherein the organism is a microorganism, yeast, or plant.

19. The gene construct of claim 3, wherein the one or more regulation signals comprise one or more promoter, terminator, or polyadenylation site.

20. The method of claim 8, which produces triglycerides having an increased content of saturated or unsaturated fatty acids as compared to an untransformed organism.

21. The method of claim 8, wherein said organism has an increased content of polyunsaturated fatty acids as compared to an untransformed organism without said nucleic acid.

22. The method of claim 21, wherein said increased content of polyunsaturated fatty acids is at least 10% increased as compared to an untransformed organism without said nucleic acid.

23. The method of claim 21, wherein said increased content of polyunsaturated fatty acids is at least 20% increased as compared to an untransformed organism without said nucleic acid.

24. The method of claim 21, wherein said increased content of polyunsaturated fatty acids is at least 40% increased as compared to an untransformed organism without said nucleic acid.

25. The method of claim 10, wherein said polyunsaturated fatty acid molecules comprise fatty acids having an increased content of Δ6-double bonds as compared to an untransformed organism.

26. An isolated nucleic acid that encodes a polypeptide having Δ6-desaturase activity, wherein the polypeptide exhibits higher Δ6-desaturase activity for ω-3 fatty acids as compared to ω-6 fatty acids, wherein said nucleic acid is derived from a plant and wherein the nucleic acid comprises a nucleotide sequence that encodes a polypeptide comprising an amino acid sequence having at least 95% identity to the amino acid sequence as set forth in SEQ ID NO: 2, wherein the polypeptide has Δ6-desaturase activity, and the polypeptide exhibits higher Δ6-desaturase activity for ω-3 fatty acids as compared to ω-6 fatty acids.

27. The isolated nucleic acid of claim 26, wherein said nucleic acid is derived from the genera *Muscariodides* or *Aleuritia*.

28. A gene construct containing the isolated nucleic acid of claim 26, wherein said nucleic acid is functionally linked to one or more regulation signals.

29. A vector containing the isolated nucleic acid of claim 26.

30. A transgenic nonhuman organism containing the isolated nucleic acid of claim 26, wherein the organism is a microorganism, yeast, or plant.

31. The transgenic nonhuman organism of claim 30, wherein said organism is a microorganism or a plant.

32. The transgenic nonhuman organism of claim 30, wherein said organism is a plant.

33. A method for producing polyunsaturated fatty acids, wherein the method comprises growing a transgenic organism which comprises the isolated nucleic acid of claim 26, wherein, due to the activity of said Δ-6 desaturase, polyunsaturated fatty acids are formed in said organism which exhibit an increased content of ω-3 fatty acids compared to a non-transformed organism, wherein the organism is a microorganism, yeast, or plant.

34. The method of claim 33, wherein stearidonic acid, eicosapentaenoic acid or docosahexaenoic acid is produced.

35. The method of claim 33, further comprising isolating polyunsaturated fatty acid molecules from said organism in the form of an oil, lipid or a free fatty acid.

36. The method of claim 33, wherein said organism is a microorganism or a plant.

37. The method of claim 33, wherein said organism is a transgenic plant.

38. The method of claim 35, wherein said polyunsaturated fatty acid molecules comprise a $C_{18}$ fatty acid having at least three double bonds.

39. The isolated nucleic acid of claim 26, wherein the Δ6-desaturase activity toward ω-3 fatty acids as compared to ω-6 fatty acids is higher by a factor of at least 1.5.

40. The isolated nucleic acid of claim 39, wherein the factor is at least 3.

41. The isolated nucleic acid of claim 39, wherein the factor is at least 5.

42. A vector containing the gene construct of claim 28.

43. A transgenic nonhuman organism containing the gene construct of claim 28, wherein the organism is a microorganism, yeast, or plant.

44. The gene construct of claim 28, wherein the one or more regulation signals comprise one or more promoter, terminator, or polyadenylation site.

45. The method of claim 33, which produces triglycerides having an increased content of saturated or unsaturated fatty acids as compared to an untransformed organism.

46. The method of claim 33, wherein said organism has an increased content of polyunsaturated fatty acids as compared to an untransformed organism without said nucleic acid.

47. The method of claim 46, wherein said increased content of polyunsaturated fatty acids is at least 10% increased as compared to an untransformed organism without said nucleic acid.

48. The method of claim 46, wherein said increased content of polyunsaturated fatty acids is at least 20% increased as compared to an untransformed organism without said nucleic acid.

49. The method of claim 46, wherein said increased content of polyunsaturated fatty acids is at least 40% increased as compared to an untransformed organism without said nucleic acid.

50. The method of claim 35, wherein said polyunsaturated fatty acid molecules comprise fatty acids having an increased content of Δ6-double bonds as compared to an untransformed organism.

* * * * *

UNITED STATES PATENT AND TRADEMARK OFFICE
CERTIFICATE OF CORRECTION

PATENT NO. : 7,554,008 B2  Page 1 of 1
APPLICATION NO. : 10/504424
DATED : June 30, 2009
INVENTOR(S) : Johnathan A. Napier et al.

It is certified that error appears in the above-identified patent and that said Letters Patent is hereby corrected as shown below:

In Claim 18, in column 37, on line 65, "trangenic" should read -- transgenic --.

Signed and Sealed this

Twenty-fourth Day of November, 2009

David J. Kappos
*Director of the United States Patent and Trademark Office*